US012684899B2

(12) United States Patent
Rienzi et al.

(10) Patent No.: US 12,684,899 B2
(45) Date of Patent: Jul. 14, 2026

(54) III-NITRIDE LED WITH UV EMISSION BY AUGER CARRIER INJECTION

(71) Applicant: The Regents of the University of California, Oakland, CA (US)

(72) Inventors: Vincent Rienzi, Santa Barbara, CA (US); Christian J. Zollner, Goleta, CA (US); Steven P. DenBaars, Goleta, CA (US); Shuji Nakamura, Santa Barbara, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 778 days.

(21) Appl. No.: 17/926,046

(22) PCT Filed: May 28, 2021

(86) PCT No.: PCT/US2021/034800
§ 371 (c)(1),
(2) Date: Nov. 17, 2022

(87) PCT Pub. No.: WO2021/243178
PCT Pub. Date: Dec. 2, 2021

(65) Prior Publication Data
US 2023/0187573 A1 Jun. 15, 2023

Related U.S. Application Data

(60) Provisional application No. 63/031,448, filed on May 28, 2020.

(51) Int. Cl.
*H10H 20/811* (2025.01)
*A61L 2/10* (2006.01)
(Continued)

(52) U.S. Cl.
CPC .............. *H10H 20/811* (2025.01); *A61L 2/10* (2013.01); *A61L 2/26* (2013.01); *C09K 11/0883* (2013.01); *C09K 11/64* (2013.01); *C09K 11/77066* (2021.01); *H10H 20/01335* (2025.01); *H10H 20/812* (2025.01); *H10H 20/824* (2025.01);
(Continued)

(58) Field of Classification Search
None
See application file for complete search history.

(56) References Cited

U.S. PATENT DOCUMENTS 8,242,522 B1 8/2012 Raring
8,575,592 B2 11/2013 Bergmann et al.
(Continued)

OTHER PUBLICATIONS

PCT International Search Report and Written Opinion dated Aug. 30, 2021 for PCT Application No. PCT/US2021/34800.

*Primary Examiner* — Nilufa Rahim
(74) *Attorney, Agent, or Firm* — Gates & Cooper LLP

(57) ABSTRACT

A III-nitride LED with simultaneous visible and ultraviolet (UV) emission, in which the visible emission is due to conventional InGaN active region mechanisms and the UV emission occurs due to Auger carrier injection into a UV light emitting region, such as impurity-doped AlGaN. The primary application for the III-nitride LED is general airborne pathogen inactivation to prevent the transmission of airborne-mediated pathogens while being safe for humans.

15 Claims, 8 Drawing Sheets

(51) Int. Cl.

| | |
|---|---|
| A61L 2/26 | (2006.01) |
| C09K 11/08 | (2006.01) |
| C09K 11/64 | (2006.01) |
| C09K 11/77 | (2006.01) |
| H10H 20/01 | (2025.01) |
| H10H 20/812 | (2025.01) |
| H10H 20/824 | (2025.01) |
| H10H 20/825 | (2025.01) |
| *A61L 103/75* | (2026.01) |

(52) U.S. Cl.

CPC ...... H10H 20/8252 (2025.01); *A61L 2103/75* (2026.01); *A61L 2202/11* (2013.01)

(56) References Cited

U.S. PATENT DOCUMENTS

| | | | | |
|---|---|---|---|---|
| 8,592,800 | B2 | 11/2013 | Moustakas et al. | |
| 8,723,189 | B1 | 5/2014 | Liao et al. | |
| 11,195,973 | B1 * | 12/2021 | Pynn | H10H 20/825 |
| 2012/0313077 | A1 | 12/2012 | Nakamura et al. | |
| 2016/0359300 | A1 | 12/2016 | El-Ghoroury et al. | |
| 2017/0084779 | A1 * | 3/2017 | Moe | H10H 20/825 |
| 2019/0346705 | A1 * | 11/2019 | Soltani | H01S 5/34333 |
| 2024/0405160 | A1 * | 12/2024 | Pandey | H10H 20/0137 |

* cited by examiner

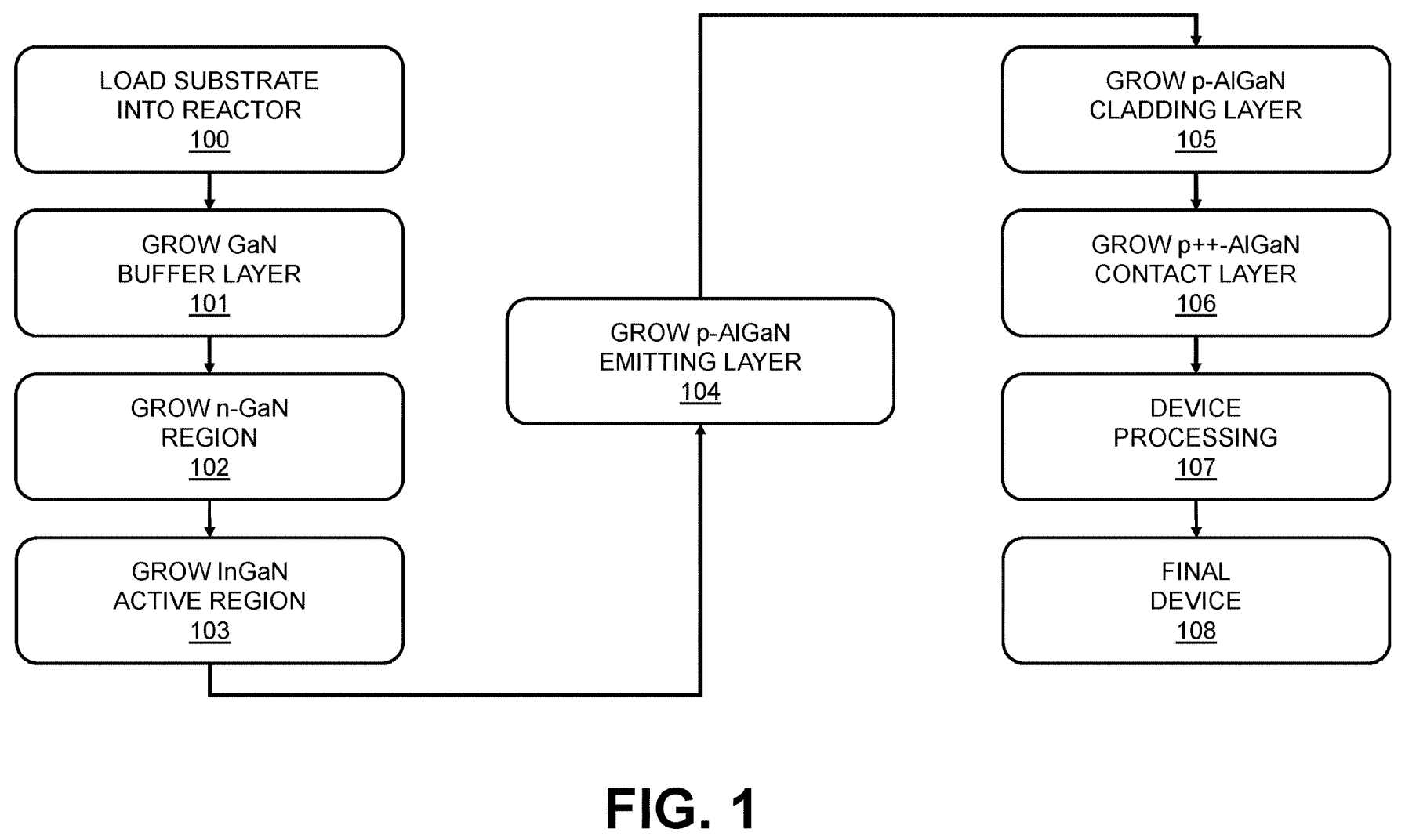

LOAD SUBSTRATE
INTO REACTOR
100

GROW GaN
BUFFER LAYER
101

GROW n-GaN
REGION
102

GROW InGaN
ACTIVE REGION
103

GROW p-AlGaN
EMITTING LAYER
104

GROW p-AlGaN
CLADDING LAYER
105

GROW p++-AlGaN
CONTACT LAYER
106

DEVICE
PROCESSING
107

FINAL
DEVICE
108

FIG. 1

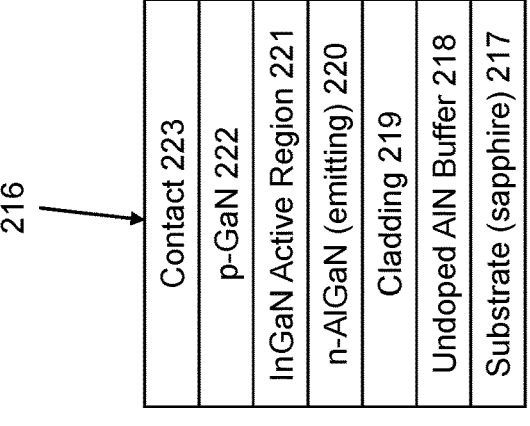
200 →
| Contact 207 |
| p-GaN 206 |
| EBL 205 |
| InGaN Active Region 204 |
| n-GaN 203 |
| Undoped GaN Buffer 202 |
| Substrate (sapphire) 201 |
FIG. 2A
208 →
| Contact 215 |
| Cladding 214 |
| p-AlGaN (emitting) 213 |
| InGaN Active Region 212 |
| n-GaN 211 |
| Undoped GaN Buffer 210 |
| Substrate (sapphire) 209 |
FIG. 2B
216 →
| Contact 223 |
| p-GaN 222 |
| InGaN Active Region 221 |
| n-AlGaN (emitting) 220 |
| Cladding 219 |
| Undoped AlN Buffer 218 |
| Substrate (sapphire) 217 |
FIG. 2C
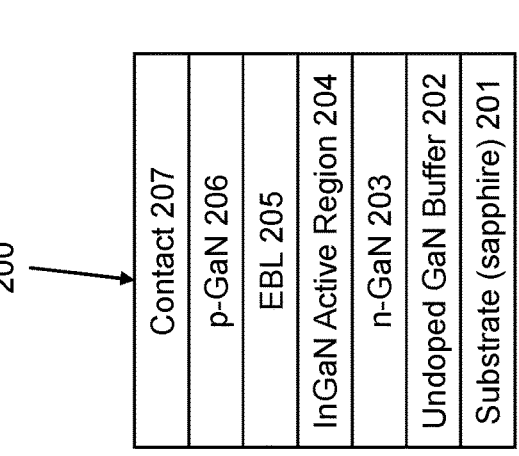

III-NITRIDE LED WITH UV EMISSION BY AUGER CARRIER INJECTION

CROSS REFERENCE TO RELATED APPLICATIONS

This application claims the benefit under 35 U.S.C. Section 119(e) of the following commonly-assigned application:

U.S. Provisional Application Ser. No. 63/031,448, filed on May 28, 2020, by Vincent Rienzi, Christian S. Zollner, Steven P. DenBaars and Shuji Nakamura, entitled "III-NITRIDE LED WITH UV EMISSION BY AUGER CARRIER INJECTION,";

which application is incorporated by reference herein.

This application is related to the following co-pending and commonly-assigned applications:

PCT International Patent Application No. PCT/US21/18329, filed on Feb. 21, 2021, by Daniel A. Cohen, Daniel Myers, Claude C. A. Weisbuch, and Steven P. DenBaars, entitled "GROUP MITT EMITTER ELECTRICALLY INJECTED BY HOT CARRIERS FROM AUGER RECOMBINATION,", which application claims the benefit under 35 U.S.C. Section 119(e) of and commonly-assigned U.S. Provisional Application Ser. No. 62/983,028, filed on Feb. 28, 2020, by Daniel A. Cohen, Daniel Myers, Claude C. A. Weisbuch, and Steven P. DenBaars, entitled "GROUP III-N LIGHT EMITTER ELECTRICALLY INJECTED BY HOT CARRIERS FROM AUGER RECOMBINATION,";

which applications are incorporated by reference herein.

BACKGROUND OF THE INVENTION

1. Field of the Invention

This invention relates to a III-nitride-based light-emitting diode (LED) device that simultaneously emits both visible and ultraviolet (UV) light. The visible light is emitted from an InGaN active region, but a novel Auger carrier injection method is proposed for injection of electrons into a wide band-gap impurity-doped AlGaN layer, for example, a p-type AlGaN layer, for emission of the UV light.

2. Description of the Related Art (Note: This application references a number of different publications as indicated throughout the specification by one or more reference numbers within brackets [x]. A list of these different publications ordered according to these reference numbers can be found below in the section entitled "References." Each of these publications is incorporated by reference herein.)

The state of the art in disinfection comprises biological and chemical agents. Antibiotics and other biochemical treatments of microbes can lead to the evolution of superbugs, which are multi-drug resistant bacteria, and chemical disinfectants, such as chlorine bleach for wastewater treatment, can be harmful for the environment. Microbes can also develop immunity to chemical treatments.

However, microbes will remain vulnerable to certain types of UV light. There are three types of UV light, namely, UV-A with a wavelength of 400-315 nm that is not absorbed by Earth's ozone layer, UV-B with a wavelength of 315-280 nm that is mostly absorbed by the ozone layer, and UV-C with a wavelength of 280-100 nm that is completely absorbed by the ozone layer and atmosphere.

Because all life on Earth has evolved without the presence of UV-C light, UV-C light is extremely effective at damaging DNA and RNA, rendering small or single-celled organisms and viruses unable to replicate. Thus, UV-C light is useful in various applications.

For example, surgical site infections occur when microbes multiply at a surgical wound to the extent that an infection develops; and UV-C light can sterilize tools and operating rooms, which can significantly reduce the infection rate.

Infectious diseases can be transmitted in public places via airborne or contact mechanisms; with a safe UV-C light source for general disinfection, the market for disinfecting lamps seamlessly integrated into general illumination products is expected to grow rapidly, as soon as a viable solid-state UV-C light source is developed.

Moreover, contaminated drinking and bathing water is linked to the transmission of diseases, such as dysentery, diarrhea, and typhoid. A stable, non-toxic, inexpensive, and efficient UV-C light source can disinfect water on a global scale that would otherwise be unsafe to drink and improve water security in developing regions.

Thus, there is a need in the art for improved methods and devices for generating UV-C light.

SUMMARY OF THE INVENTION

The present invention discloses a III-nitride-based LED emitting both visible and UV light, with UV emission by Auger carrier injection. This device comprises a semiconductor layer stack grown on or above a substrate, which is then fabricated into an LED device using standard semiconductor processing technologies.

BRIEF DESCRIPTION OF THE DRAWINGS

Referring now to the figures in which like reference numbers represent corresponding parts throughout:

FIG. 1 is a process flowchart that illustrates the steps for the growth and fabrication of a III-nitride LED according to an embodiment of the invention.

FIG. 2A is a schematic representation of a conventional III-nitride InGaN-based. LED with an emission wavelength of 370 nm-460 nm comprising blue/violet light.

FIG. 2B is a schematic representation of a III-nitride LED including a UV light emitting LED epi stack on a blue/violet light emitting LED epi stack.

FIG. 2C is a schematic representation of a III-nitride LED including a UV light emitting LED epi stack below a blue/violet light emitting LED epi stack.

US 12,684,899 B2

3

DETAILED DESCRIPTION OF THE INVENTION

Figure 3A:
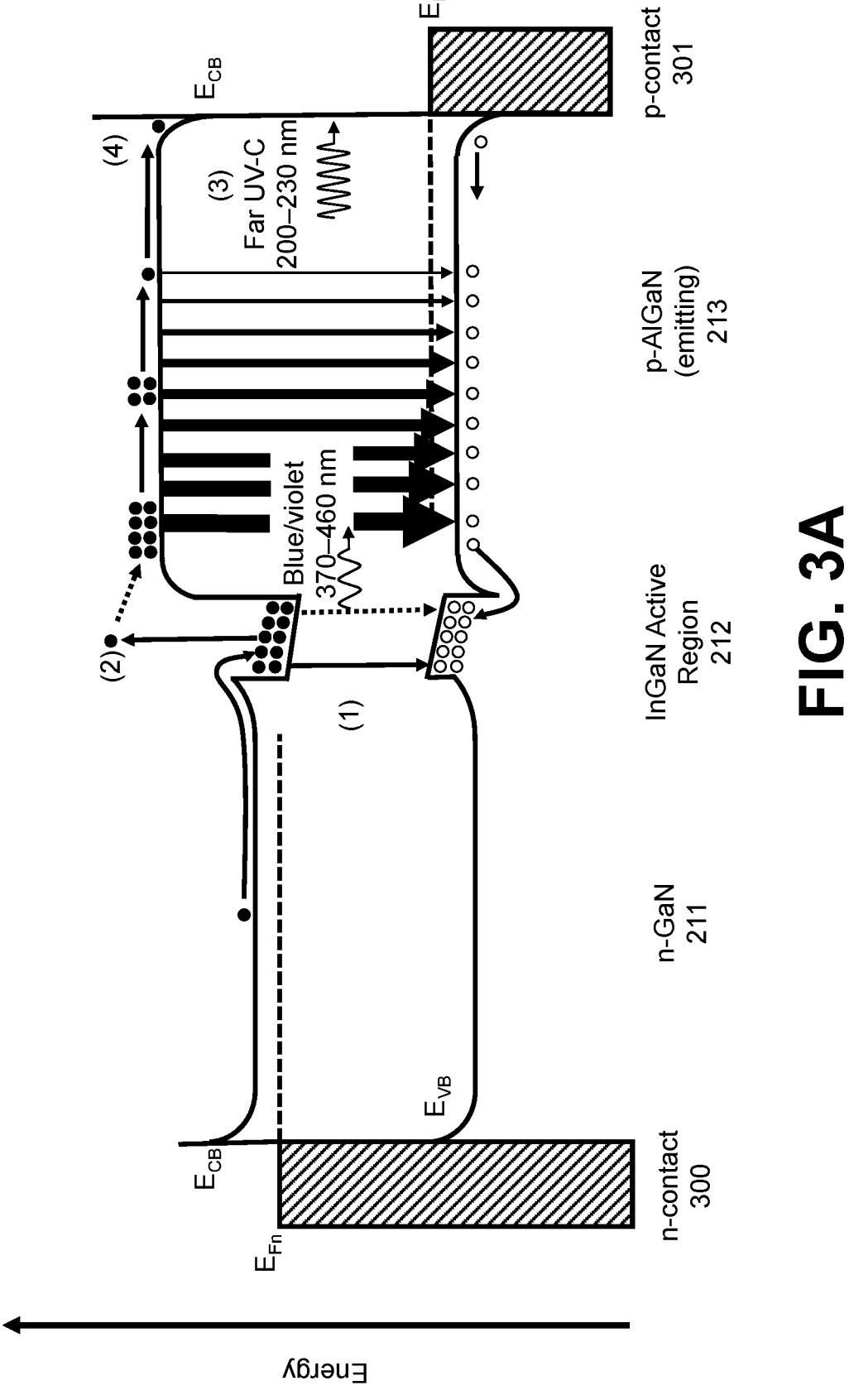
FIG. 3A is an energy band diagram for a proposed LED under forward bias that depicts possible pathways for electrons and holes in the device.

In the following description of the preferred embodiment, reference is made to the accompanying drawings which form a part hereof, and in which is shown by way of illustration a specific embodiment in which the idea may be practiced. It is to be understood that other embodiments may be utilized, and structural changes may be made without departing from the scope of the present invention.

Overview

The present invention describes a far UV-C LED that is electrically injected through Auger processes. In particular, this invention discloses a device with two emitting regions: a blue to violet (InGaN) emitting region which operates in a manner typical of conventional III-nitride LEDs, and a far UV-C (impurity-doped. AlGaN) emitting region in which hot carriers escaping the InGaN emitting region via Auger processes recombine radiatively in the impurity-doped AlGaN emitting region. The far UV-C impurity-doped AlGaN emitting region may be located on the p-side of the InGaN emitting region, where the majority of Auger-generated hot electrons are expected to recombine radiatively. Alternatively, the far UV-C impurity-doped AlGaN emitting region may be located on the n-side of the InGaN emitting region, where the majority of Auger-generated hot holes are expected to recombine radiatively.

In a typical III-nitride LED with a single emitting region, electrons are confined in the InGaN active region by InGaN quantum wells (QWs) and electron blocking layer (EBL) structures, so that visible radiative recombination dominates at relatively low current densities.

However, at increased current densities (thus, high carrier densities), a significant fraction of carriers [1] undergo Auger processes in the violet/blue InGaN active region, giving them enough energy to escape the active region of the device. This is conventionally interpreted as a detrimental effect because the internal quantum efficiency of the violet/blue LED is reduced.

The present invention, however, aims to harness these high energy carriers to emit UV light for disinfecting applications, wherein the UV emission is achieved by electron-hole recombination occurring in the impurity-doped AlGaN emitting region. The impurity-doped AlGaN emitting region may comprise one or more AlGaN:Mg layers, which are p-type AlGaN (p-AlGaN) layers, graded p-AlGaN layers, p-AlGaN multiple quantum well (MQW) layers, or any combination thereof. In an alternative embodiment, the impurity-doped AlGaN emitting region may comprise one or more AlGaN:Si layers, which are n-type AlGaN (n-AlGaN) layers, graded n-AlGaN layers, n-AlGaN MQW layers, or any combination thereof, as well as other impurity-doped AlGaN layers. In another possible embodiment, the AlGaN regions may contain some Sc, so that they may be referred to as AlGaScN regions, as defined below. In the present disclosure, the term "AlGaN" will be used to describe the ultrawide bandgap, UV-emitting regions, while it is to be understood that in an alternative embodiment any ultrawide bandgap nitride semiconductor as defined below may be used.

The increased bandgap of AlGaN alloys allows Auger-generated hot electrons or holes injected into AlGaN layers to radiatively recombine and produce far UV-C light. The band gap, $E_g$, of $Al_xGa_{1-x}N$ can be calculated using the following equation:

$$E_g=3.42 \text{ eV}+x2.86 \text{ eV}-x(1-x)1.0 \text{ eV}$$

4

For far UV-C emission, this corresponds to Al compositions of x=0.75 (75%) for 230 nm emission and x=0.98 (98%) for 200 nm emission.

The resulting device may replace conventional white light emitting LEDs in lighting fixtures, which emit blue light originating from an InGaN/GaN active region and have a phosphor coating to convert some of the blue light to yellow light through fluorescence, due to the added benefit of acting as a safe and effective antimicrobial by emitting far UV-C light. Alternatively, this device may be installed alone or together with conventional white light emitting LEDs in lighting fixtures to act as a safe and effective antimicrobial.

Technical Description

This invention relates to the fabrication of devices using III-nitride-based semiconductors layers. As used herein, the term "III-nitride," or more simply "nitride," refers to any alloy composition of the (Ga,Al,In,B,Sc)N semiconductors having the formula $Ga_nSc_wAl_xIn_yB_zN$ where:

$0{\le}n{\le}1, 0{\le}w{\le}1, 0{\le}x{\le}1, 0{\le}y{\le}1, 0{\le}z{\le}1$, and n+w+x+y+z=1.

The III-nitride layers may comprise single or multiple layers having varied or graded compositions, including layers of dissimilar (Al,Ga,In,B,Sc)N composition. Moreover, the layers may also be doped with elements such as silicon (Si), germanium (Ge), magnesium (Mg), boron (B), iron (Fe), oxygen (O), and zinc (Zn).

The III-nitride layers are grown on a substrate, which may comprise sapphire, SiC, or some other substrate. The substrate may also comprise GaN or another nitride substrate, or a lattice matched template or strain-relieved template (pseudo-substrate) on a foreign substrate.

The substrate may have a growth surface that is polar c-plane oriented, or nonpolar a-plane or m-plane oriented, or semipolar plane oriented, such as the {20-21}, {11-22}, {10-11} planes. The growth surface of the substrate may be chemo-mechanically or otherwise polished to provide an atomically flat surface, where atomic step-terraces are present.

The III-nitride layers may be grown on the substrate in any crystallographic direction such as on a conventional polar c-plane or on a nonpolar plane, such as an a-plane or m-plane, or on any semipolar plane, such as {20-21}, {20-2-1}, {11-22}, or {10-11}.

The III-nitride layers may be grown using deposition methods such as metalorganic chemical vapor deposition (MOCVD), hydride vapor phase epitaxy (HVPE) or molecular beam epitaxy (MBE).

The usefulness of III-nitride layers, such as gallium nitride (GaN), and its ternary and quaternary compounds incorporating aluminum and indium (AlGaN, InGaN, AlInGaN), has been well established for the fabrication of visible and ultraviolet optoelectronic devices and high-power electronic devices.

Additionally, the development of AlGaN for short wavelength devices has enabled III-nitride-based LEDs and laser diodes (LDs). Consequently, AlGaN based materials and devices have become the dominant material system used for ultraviolet light semiconductor applications.

Efficiency droop is observed at high carrier or current densities in LEDs where the device efficiency decreases with increasing carrier or current densities. This decrease is primarily attributed to Auger recombination [2,3], which results in high energy electrons or holes escaping the active region into the p-side or n-side, respectively, of the device.

Auger recombination is a process by which a conduction band electron drops to the valence band, releasing energy approximately equal to the band gap energy ($E_g$ of InGaN active layer) to excite another electron in the conduction band to a higher energy level without photon emission. Through this process, the electron has energy equal to about $2E_g$ above the valence band, and is called a hot electron. This process is known as electron-electron-hole (eeh) Auger recombination. Alternatively, Auger recombination may occur when a conduction band electron drops to the valence band, releasing energy approximately equal to the band gap energy ($E_g$ of InGaN active layer) to excite a hole in the valence band to a higher energy level without photon emission. Through this process, the hole has energy equal to about $E_g$ below the valence band (in the case of electron-hole-hole (ehh) Auger recombination), and is called a hot hole.

In typical visible light emitting LED devices, hot electrons (or holes) may recombine nonradiatively in the p-side (n-side) of the device or diffuse to the metal contact (resulting in leakage current and efficiency droop). Using the novel structure of the present invention, hot carriers generated by Auger processes in a violet/blue light (370 nm-460 nm) emitting InGaN active layer have sufficient energy to produce photon emission of far UV-V light (200 nm-230 nm).

For efficient radiative recombination of electron-hole pairs in a semiconductor light emitting diode, there must exist: (1) an energy difference between electrons and holes (e.g. the band gap of the semiconductor), and (2) a very small or negligible momentum difference, so that photon emission may occur in accordance with conservation of momentum.

Within semiconductor band structures, a gap meeting these two criteria constitutes a direct gap, wherein the direct gap existing at the Γ-point of InGaN yields very efficient electron-hole recombination. In contrast, the gap between the valence and conduction bands of Si and Ge is indirect, meaning that a significant momentum difference exists between the relevant electron and hole states, and radiative recombination is negligible.

In the case of an InGaN and p-GaN heterojunction, electrons originating in the InGaN conduction band (i.e., the Γ-valley) and excited via Auger processes predominantly scatter via phonon scattering into the L-valley of p-GaN [3]. Therefore, even when significant population of the L-valley occurs, the indirect nature of the gap between the L-valley electrons and Γ-valley holes greatly reduces radiative recombination.

On the other hand, in the case of an InGaN and p-AlGaN heterojunction, hot electrons generated in the InGaN active region have energy $2E_{g, InGaN} \approx E_{g, AlGaN}$, allowing them to scatter efficiently into the Γ-conduction band of p-AlGaN. More specifically, the Auger-generated hot electrons gain energy $E_{g, InGaN}$ above the InGaN conduction band, which is greater than or approximately equal to the conduction band offset between the InGaN and AlGaN layers, allowing them to efficiently populate the Γ-valley in AlGaN. The high rate of hot-electron generation and subsequent population of the p-AlGaN conduction band via diffusion leads to high rates of radiative recombination with valence band holes due to the direct nature of this Γ-Γ energy gap.

This same analysis can be applied to the case of an InGaN and n-AlGaN heterojunction, where hot holes generated in the InGaN active region have energy $E_g$ below the InGaN valence band, allowing them to scatter efficiently into the Γ-valence band of n-AlGaN. Similar to hot electrons, the Auger generated hot holes gain energy $E_g$ below the InGaN valence band maximum, which is greater than or approximately equal to the valence band offset between the InGaN and AlGaN layers, allowing them to efficiently populate the valence band maximum in AlGaN. The high rate of hot-hole generation and subsequent population of the n-AlGaN valence band via diffusion leads to high rates of radiative recombination with conduction band electrons due to the direct nature of this Γ-Γ energy gap.

In summary, in order to utilize the hot carriers from Auger processes to produce UV-C light, impurity-doped-AlGaN may be used. When p-GaN is used, little or no light may be emitted due to the indirect energy band gap for hot electrons populating higher-energy conduction band valleys.

The volume of the InGaN active region should be small to achieve a high carrier density at a low or moderate operating current. The thinner the InGaN active region, the higher the carrier density, and therefore the greater the Auger recombination rate becomes, which is proportional to $N^3$ ($N$=total carrier density). A single quantum well (SQW) with a thickness less than 5 nm would be the best for the InGaN active region.

Epitaxial growth of many semiconductors such as AlGaAs, InGaAsP, and others, benefits from the controllable growth of so-called lattice matched heterostructures. In such structures, layers with differing composition (e.g. AlGaAs and GaAs) have nearly the same relaxed in-plane lattice parameter, so that heterostructures of dissimilar bandgap, refractive index, electrical polarization, or other property, may be grown with very low strain. This improves device performance and structural quality. In contrast, lattice-mismatched structures comprise regions with differing relaxed in-plane lattice parameter, and therefore at least one region is under elastic strain when these regions are joined epitaxially in heterostructures. This strain can lead to degraded optical performance and structural defects.

There is a relatively large lattice mismatch between blue/violet InGaN and far UV-C AlGaN alloys. When these materials are coherently grown together in thin film structures, large biaxial stress results. For AlGaN regions grown on or above an InGaN region, the AlGaN is under biaxial tension which can lead to cracking and is detrimental to device performance. When InGaN is grown on or above AlGaN, the InGaN experiences biaxial compression, which, while being less severe than biaxial tension, still leads to a significant reduction in device efficiency, To alleviate the strain between these highly lattice mismatched layers, Sc-containing nitride layers with modified lattice constants can be incorporated. For example, ScAlN could be used instead of AlGaN as the UV emitting layer for this invention.

It is well established that UV light less than 300 nm is an effective disinfectant of airborne microbes. Conventional germicidal UV-C light sources utilize toxic mercury vapor lamps and operate at wavelengths greater than 250 nm. These wavelengths are cataractogenic for eyes and carcinogenic for exposed skin because the radiation is weakly absorbed by the outer layer of dead cells and damages living cells. Far UV-C light with emission wavelengths of 200 nm-230 nm is neither cataractogenic nor carcinogenic due to strong absorption by the outer layer of dead cells [4,5], while still being strongly germicidal. Thus, far UV-C light would be the best for disinfection applications.

Besides toxic and harmful mercury lamp sources, other prior art UV light sources include excimer lasers using KrBr* and KrCl* radicals. These lasers do not have the benefit of semi-spherical light output like LEDs do; rather, they are highly directional. Also, lasers cannot be used with humans present because it creates an eye safety problem. There is strict regulation of laser usage in public settings. These devices are therefore not well suited for general disinfection applications.

US 12,684,899 B2

7
8

Flowchart

FIG. 1 is a flowchart that illustrates the steps for the fabrication of a III-nitride-based light emitting structure having both a visible light emitting region and a UV light emitting region, wherein UV light emission is generated by Auger carrier injection into the UV light emitting region, according to one embodiment of the invention.

Block 100 represents the step of loading a sapphire substrate, which may be atomically flat or step-prepared, into a reactor, such as an MOCVD reactor.

Block 101 represents the step of growing a nominally undoped GaN buffer layer on or above the substrate. This is achieved by flowing Ga and N precursors sequentially into the reaction chamber. Possible precursors for Ga and N include TMGa and NH$_3$, respectively.

Block 102 represents the step of epitaxially growing an n-GaN region on or above the nominally undoped GaN buffer layer. The n-GaN region may be comprised of one or more layers, including superlattice(s), multilayered, compositionally graded, or other nitride layers.

Block 103 represents the step of epitaxially growing an InGaN active region on or above the n-GaN region, wherein the InGaN active region emits visible violet and/or blue light, i.e., has an emission wavelength of 370 nm-460 nm. For simplicity, the InGaN active region is depicted as a SQW, wherein the SQW has a thickness of less than 5 nm. However, the InGaN active region may comprise MQWs, other multilayer structures, or graded layers. The InGaN active region is optimized for maximum Auger recombination, for example, by maximizing confinement into a small volume to achieve the greatest possible carrier density at a given current density.

Block 104 represents the step of epitaxially growing a UV light emitting region on or above the InGaN active region, wherein the UV light emitting region comprises impurity-doped AlGaN and the impurity-doped AlGaN comprises one or more p-AlGaN emitting layers; however, in alternative embodiments, the p-AlGaN emitting layer may comprise p-AlGaN quantum well(s), graded layer(s), superlattice(s), or other layer structures. The UV light emitting region preferably has an emission wavelength below 310 nanometers (UV-B), more preferably below 280 nanometers (UV-C), and most preferably between 200-230 nanometers (far UV-C).

Block 105 represents the optional step of epitaxially growing p-AlGaN cladding layer(s) on a p-side of the device on or above the p-AlGaN emitting layer, wherein the p-AlGaN cladding layers have a wider band gap than the p-AlGaN emitting layer. The p-AlGaN cladding layer's purpose is to confine electrons in the p-AlGaN emitting layer, to reduce electron overflow from the p-AlGaN emitting layer, and to provide a transparent or mostly transparent layer through which UV-C light may be extracted. These p-AlGaN cladding layers may have a higher Al content than the p-AlGaN region, superlattice(s), graded, or other layer structures; in addition, the cladding layers may be omitted.

Block 106 represents the step of epitaxially growing one or more p-side contact layer(s) on a p-side of the device on or above the p-AlGaN emitting layer and the p-AlGaN cladding layer. The p-side contact layers comprise a highly Mg doped p++-AlGaN region, p++ GaN region, or p++-AlN hole-gas. These contact layers include a much higher Mg concentration than the p-AlGaN emitting layer and the p-AlGaN cladding layer in order to make a good Ohmic contact with a variety of metals, oxides, and other materials. These contact layers may comprise one or more p++-AlGaN layer(s), superlattice(s), graded layer(s), or other layer structures. The contact layers should be relatively thin so as to minimize absorption of UV light, e.g., the thickness of the contact layers should be less than about 20 nm.

Block 107 represents the step of processing the semiconductor layers into an LED device and then packaging the device. This may include, but is not limited to, coating or partial coating with a phosphor for conversion of blue light to yellow light, wire bonding, glass, quartz and other UV-C transparent encapsulation, and inspection. The device may also be installed in the lighting fixture.

Block 108 represents the end result of the method, namely, a III-nitride-based light emitting structure having both a visible light emitting region and a UV light emitting region, for example, a III-nitride LED capable of simultaneous visible and far UV-C emission, wherein the visible light emitting region is an InGaN active region emitting violet and/or blue light; the UV light emitting region comprises impurity-doped AlGaN and the impurity-doped AlGaN comprises one or more p-AlGaN layers; and Auger recombination processes lead to generation of high-energy hot electrons in the InGaN active region and the hot electrons transport into the p-AlGaN layers where the hot electrons recombine to emit UV light.

The above steps may be modified, eliminated, repeated, or completed in any desired order, without departing from the scope of the present invention.

Device Structures

FIG. 2A is a schematic representation of the epitaxial layers of a conventional III-nitride InGaN-based LED 200 emitting visible blue/violet light with an emission wavelength of 370 nm-460 nm. In this embodiment, the LED 200 is comprised of a sapphire substrate 201, upon which is grown an undoped GaN buffer layer 202, n-GaN 203, InGaN active region 204, EBL 205, p-GaN 206, and contact layer 207. It is to be understood that, while illustrated as uniform layers for simplicity, many of these layers may actually comprise superlattice or multilayer structures.

When operated at low to moderate current densities, most electrons recombine radiatively in the InGaN MQW active region 204 to produce visible light. When operated at high current density, Auger recombination becomes the dominant mechanism, and the LED 200 efficiency diminishes (droop).

FIG. 2B presents a schematic of the epitaxial layers of an LED 208 comprised of a UV light emitting III-nitride LED epi stack on a blue/violet light emitting III-nitride LED epi stack, according to a preferred embodiment of the invention. In this embodiment, the LED 208 is comprised of a sapphire substrate 209, upon which is grown an undoped GaN buffer layer 210, n-GaN layer 211, InGaN active region 212, p-AlGaN (emitting) layer 213, cladding layer 214, and contact layer 215.

In this LED 208, the p-AlGaN (emitting) layer 213 is adjacent to the InGaN active region 212, rather than the typical p-GaN layer 206, wherein the p-AlGaN (emitting) layer 213 is used as the UV light emitting region.

At relatively high current or carrier densities, electrons are efficiently injected into the p-AlGaN (emitting) layer 213 via Auger processes where they may recombine radiatively to produce the UV-C light. The p-AlGaN (emitting) layer 213 may be comprised of an MQW structure to increase the radiative recombination.

On or above the p-AlGaN (emitting) layer 213, an optional cladding layer 214 is grown, followed by the contact layer 215. The cladding layer 214 serves multiple purposes: (1) it prevents electron overshoot into the p-contact layer, and (2) it provides a transparent or mostly transparent layer through which UV light may be extracted.

In the preferred embodiment, the contact layer 215 is p++-AlGaN with high Mg doping for Ohmic contact.

FIG. 2C presents a schematic of the epitaxial layers of an LED 216 comprised of a UV emitting III-nitride LED epi stack below a blue/violet light emitting III-nitride LED epi stack, according to an alternative embodiment of the invention. In this embodiment, the LED 216 is comprised of a sapphire substrate 217, upon which is grown an undoped AlN buffer layer 218, cladding layer 219, n-AlGaN (emitting) layer 220, InGaN active region 221, p-GaN layer 222, and contact layer 223.

In this embodiment, the UV emitting III-nitride LED epi stack is formed below the blue/violet light emitting III-nitride LED epi stack, unlike FIG. 2B which has the UV emitting III-nitride LED epi stack formed on or above the blue/violet light emitting III-nitride LED epi stack. Similarly, the cladding layer 219 is grown below the n-AlGaN (emitting) 220 layer rather than on or above it to prevent hole overshoot into the n-contact layer.

FIG. 3A is an energy band diagram for an LED device of this invention under forward bias, wherein the diagram depicts possible pathways for electrons (solid circles) and holes (hollow circles) in the device. The conduction band offset, valence band offset, or both may not be to scale and are intended to schematically demonstrate the concepts pertaining to the present invention. At the bottom of the diagram, elements of the LED device are labeled as n-contact 300, n-GaN layer 211, InGaN active region 212, p-AlGaN (emitting) 213, and p-contact 301.

UV light emission occurs in the p-AlGaN (emitting) layer 213 from Auger injected electrons. The possible electron paths are numbered: (1) blue/violet light emission through direct recombination in the MQW active region 212; (2) Auger recombination leading to hot electron injection; (3) UV-C light emission primarily from Auger injected electrons recombining in the p-AlGaN (emitting) layer 213. In this figure, the metal Ohmic p-contact 301 is directly deposited on the p-AlGaN (emitting) layer 213. Because electron transport in a p-type region is diffusion limited, electrons injected into the p-AlGaN (emitting) layer 213 form a concentration gradient, such that most emission occurs near the visible MQW active region 212. The recombination arrow width within the p-AlGaN (emitting) layer 213 represents the possible relative UV-C emission intensity for a given location within the emitting layer 213.

Figure 3B:
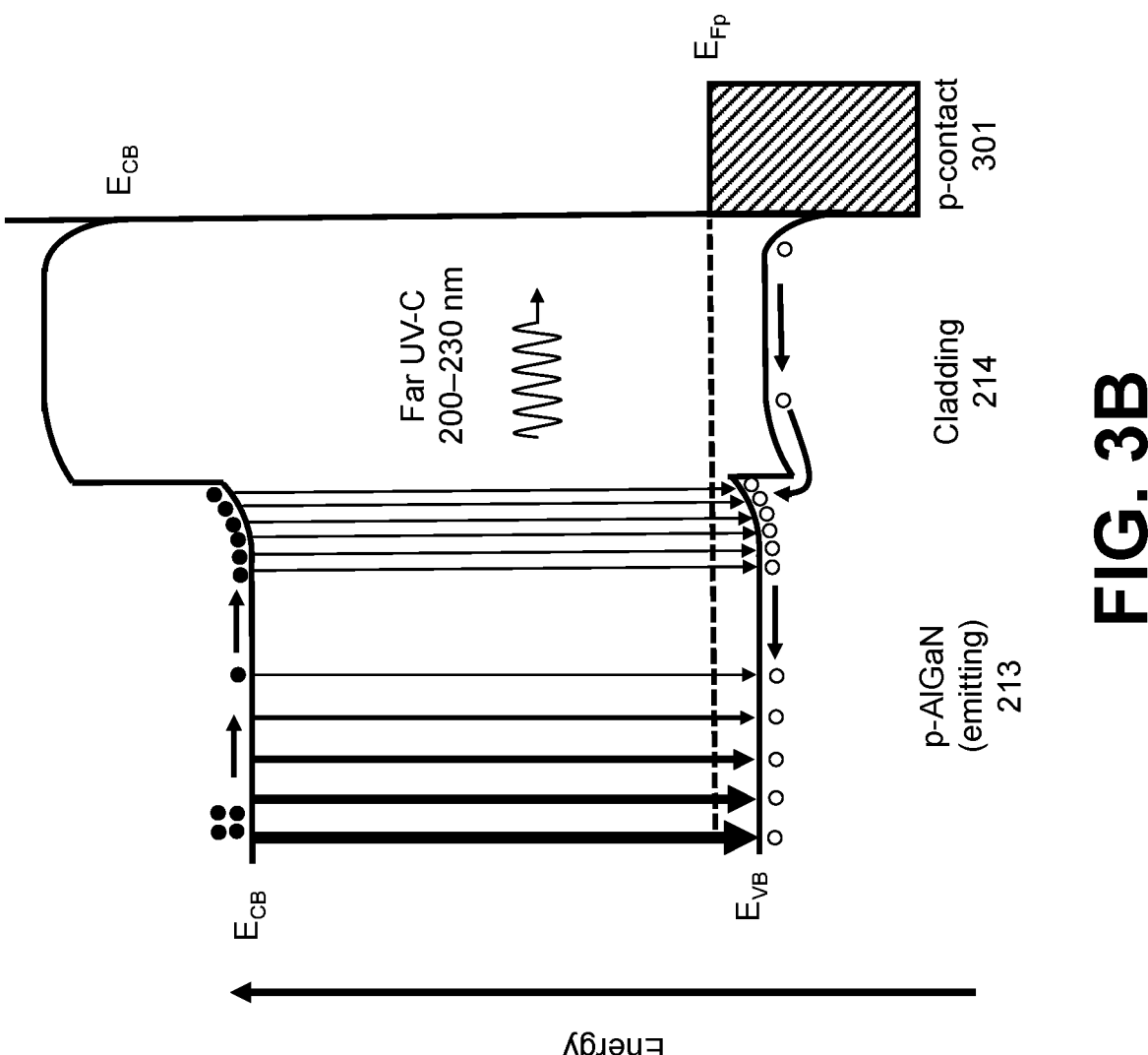
FIG. 3B shows a cladding layer grown on an p-AlGaN emitting layer.
Figure 3C:
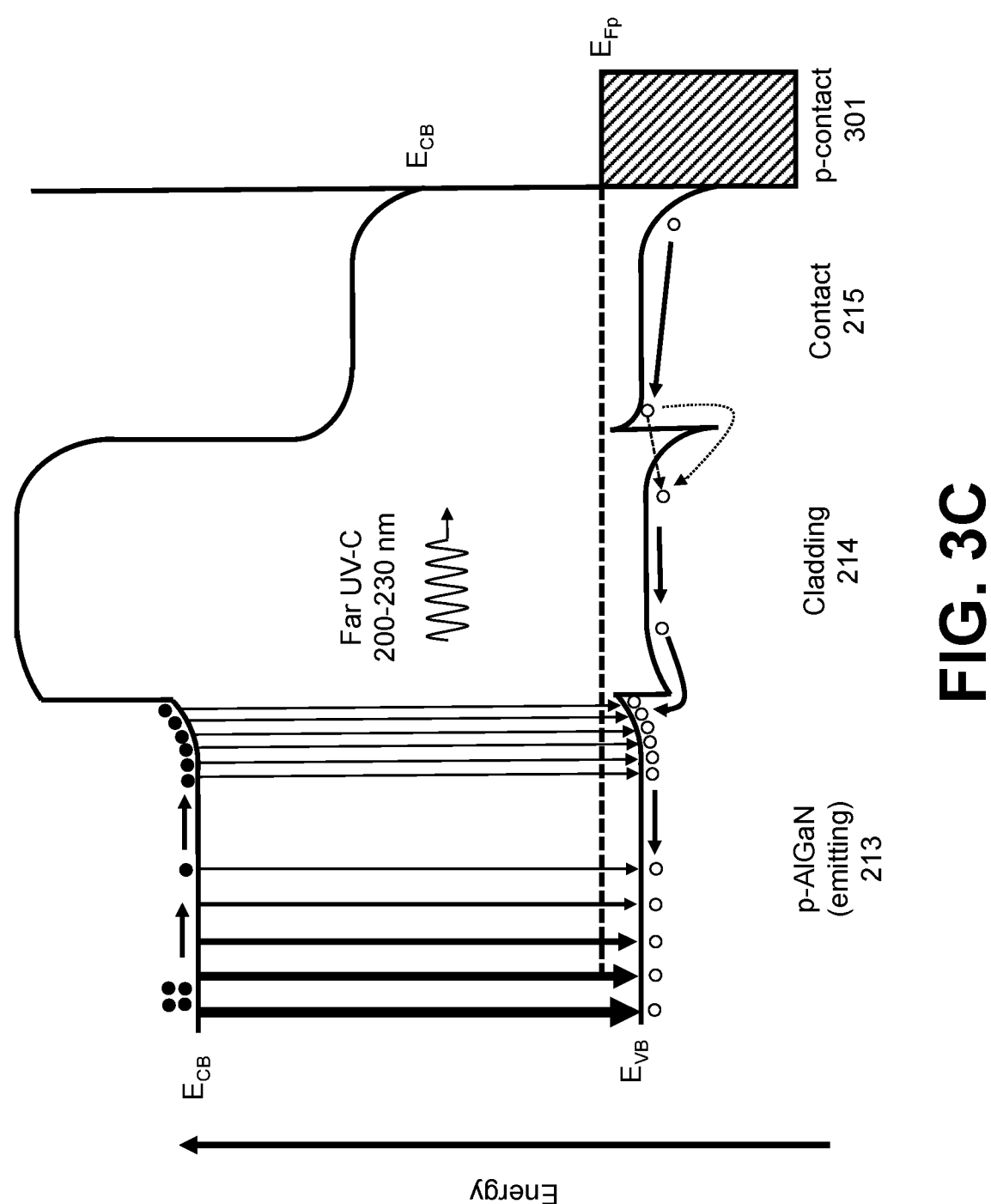
FIG. 3C shows a contact layer grown on the p-AlGaN cladding layer.

FIG. 3B is an energy band diagram for an LED device of this invention, showing the p-AlGaN (emitting) layer 213, cladding layer 214, and p-contact 301, while FIG. 3C is an energy band diagram for an LED device of this invention, showing the p-AlGaN (emitting) layer 213, cladding layer 214, contact layer 215 and p-contact 301. The cladding layer 214 may be a p-AlGaN region with a higher Al content than the p-AlGaN (emitting) layer 213, superlattice(s), graded layer(s), or other layer structures. The contact layer 215 may comprise p-AlGaN of various doping levels, superlattice(s), graded layer(s), or other layer structures.

FIG. 3B shows the p-side of the energy band for the p-AlGaN cladding layer 214 grown on the p-AlGaN (emitting) layer 213. The p-AlGaN cladding layer 214 has a higher energy band gap than the p-AlGaN (emitting) layer 213 in order to confine the hot electrons in the p-AlGaN (emitting) layer 213, thus increasing UV emission intensity.

FIG. 3C shows an energy band diagram for the contact layer 215 grown on the p-AlGaN cladding layer 214, which is grown on the p-AlGaN (emitting) layer 213. The contact layer 215 is a highly Mg doped p++-AlGaN or p++-GaN region. The purpose of the contact layer 215 is to make an Ohmic contact with metals, oxides, and other materials of the p-contact 301.

Figure 3D:
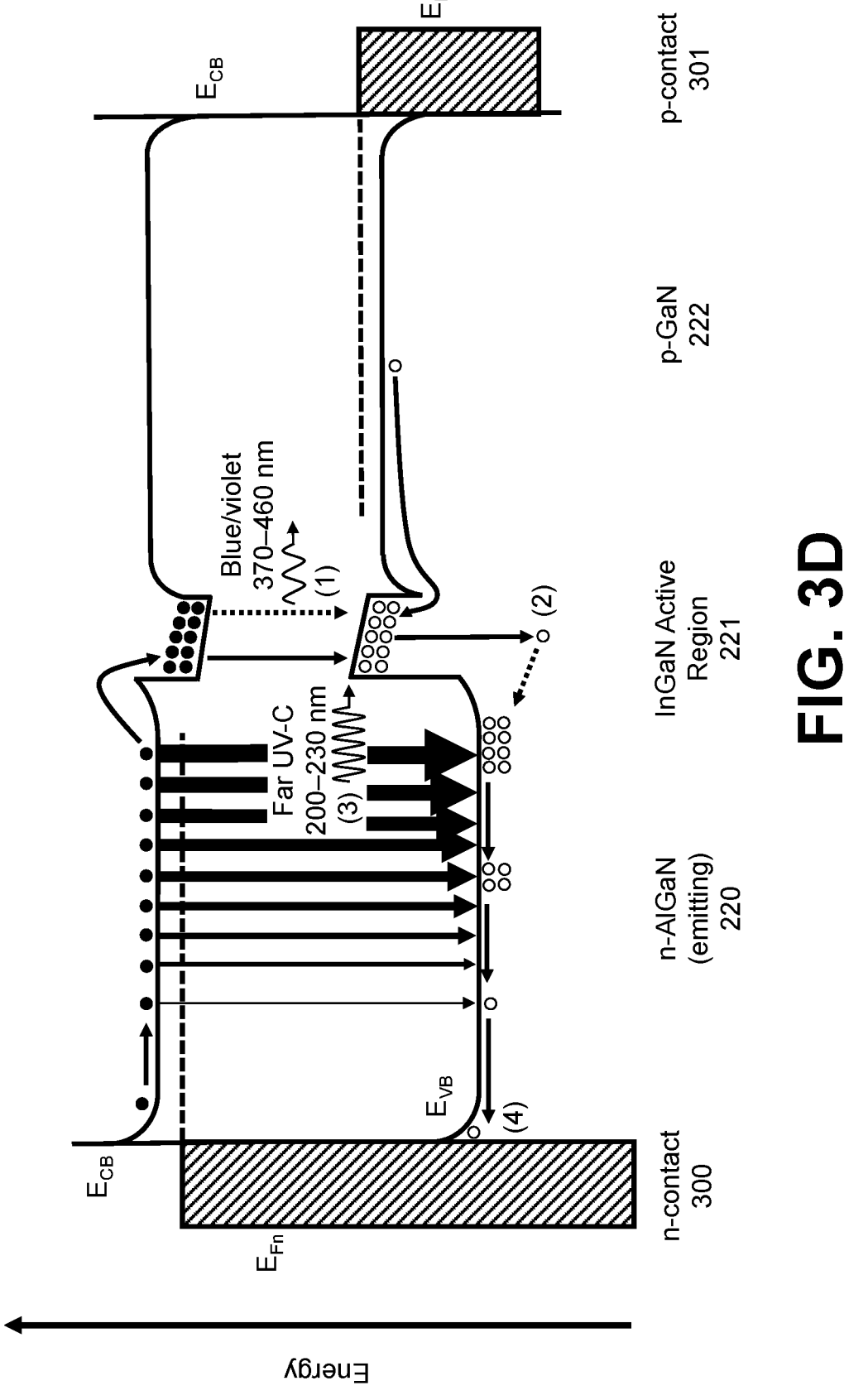
FIG. 3D is an energy band diagram for an alternative embodiment of the Auger-injected LED under forward bias that depicts alternative pathways for electrons and holes in the device.

FIG. 3D is an energy band diagram for an LED device of a possible alternative embodiment of this invention, wherein the epitaxial stack sequence is altered from FIG. 3A to be: n-AlGaN 220, InGaN active region 221, and p-GaN 222. The conduction band offset, valence band offset, or both may not necessarily be to scale and are intended to schematically demonstrate the concepts pertaining to the present invention. At the bottom of the diagram, elements of the LED device are labeled as n-contact 300, n-AlGaN (emitting) 220, InGaN active region 221, p-GaN layer 222, and p-contact 301.

FIG. 3D is analogous to FIG. 3A, except FIG. 3D shows UV light emission from the n-AlGaN (emitting) 220 from Auger injected holes rather than FIG. 3A's UV light emission occurring in the p-AlGaN (emitting) 213 from Auger injected electrons. These illustrations depict only some of the multitude of possible device architectures to optimize light emission.

Applications

Figure 4:
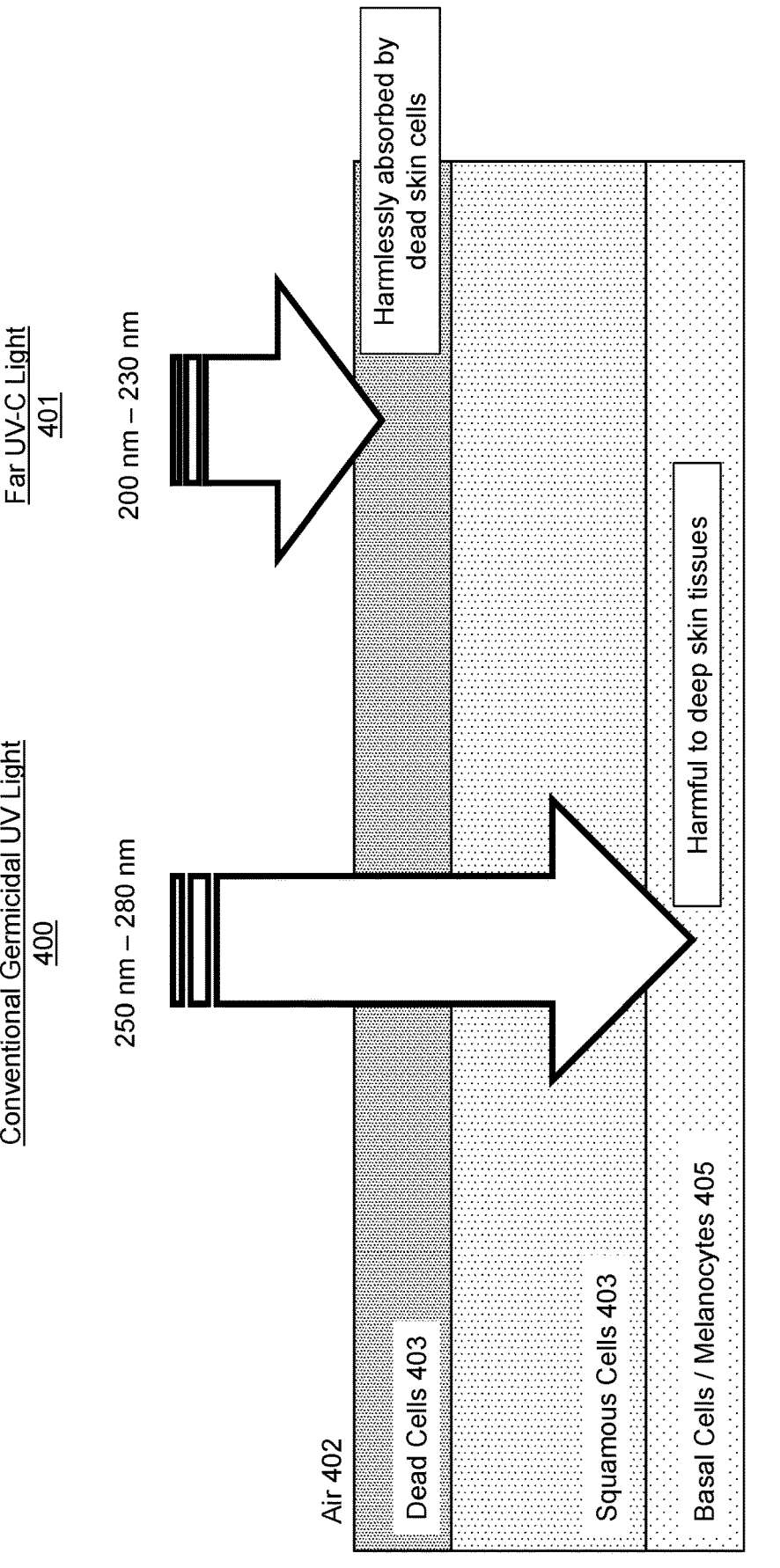
FIG. 4 depicts conventional germicidal UV light penetration into living cells, in contrast to far UV-C light which does not penetrate through the top layer of dead skin.

FIG. 4 depicts penetration of conventional germicidal UV light 400 (250 nm-280 nm), having a longer wavelength in contrast to far UV-C light 401 (200 nm-230 nm), with regard to air 402 and living cells 403, 404, 405. The far UV-C light 401 does not penetrate through the top layer of dead cells 403, while the conventional germicidal UV light 400 penetrates through the top layer of dead cells 403, squamous cells 404 and basal cells/melanocytes 405.

Both the conventional germicidal UV light 400 and far-UV-C light 401 have been proven to disinfect air 402 and surfaces of viral and bacterial pathogens. However, conventional germicidal UV light 400 penetrates human skin 403, 404, 405 deeply enough to cause damage, limiting disinfection applications to those where no humans are present. Far-UV-C light 401 is strongly absorbed by dead cells 403 at the surface of the skin, so that it is harmless to living cells 404, 405 underneath the surface of the skin.

Figure 5:
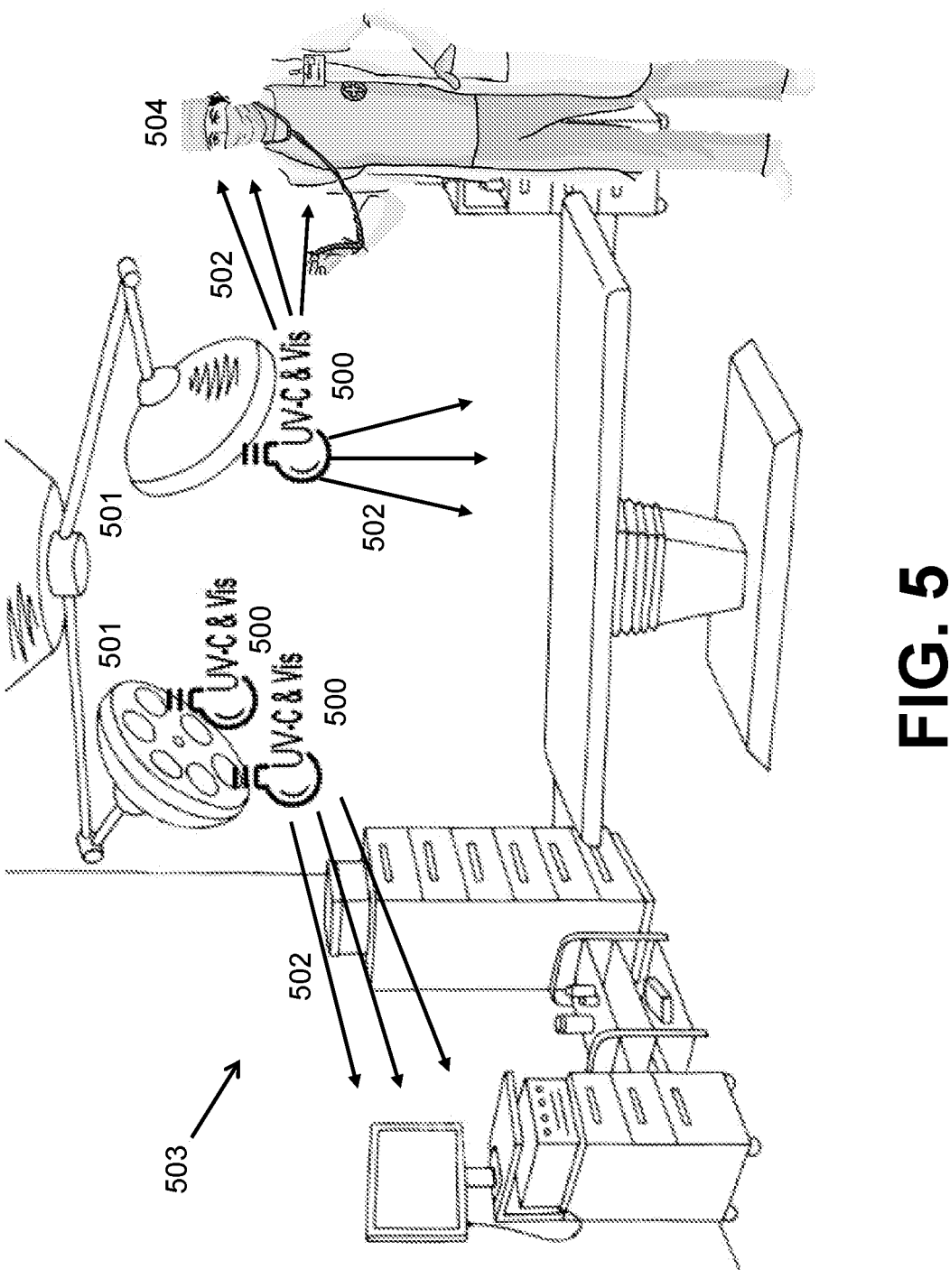
FIG. 5 shows one of many potential applications, wherein the device is installed as a lighting fixture within surgical rooms for disinfection without harming patients or medical workers.

FIG. 5 shows one of many potential applications, wherein devices 500 of the present invention are installed in lighting fixtures 501 and emit both UV-C and visible (vis) light 502 within a medical or surgical room 503 for disinfection of: (1) shared tools and electronics, (2) operating tables, beds, chairs, and other surfaces, (3) surgical masks, scrubs, and other personal protective equipment (PPE) donned by patients or medical personnel 504, and (4) doors, doorknobs, and any other commonly touched surfaces.

Unlike with conventional UV-C disinfection at wavelengths above 230 nm, novel far-UV-C disinfection technology allows humans 504 to be present during disinfection. In an alternative embodiment, conventional longer-wavelength UV-C light could be used, as long as no humans 504 are present at the time of disinfection.

Advantages

The present invention discloses a novel UV-C emitting device wherein carrier injection into the impurity-doped. AlGaN UV-C emitting layer occurs via Auger processes. The present invention includes a p-AlGaN emitting layer embedded within the p-side of the violet/blue LED device and an n-AlGaN emitting layer embedded within the n-side of the violet/blue LED device. In the preferred embodiment, impurity-doped AlGaN is used to emit far UV-C radiation with a wavelength ranging from 200 nm-230 nm. Auger recombination has been identified as the primary mechanism for efficiency droop in blue/violet LEDs at relatively high current carrier densities. This invention utilizes Auger-generated hot electrons (or holes) to diffuse to the p-AlGaN (n-AlGaN) emitting layer with a higher band gap energy and radiatively recombine with holes (electrons) to emit far UV-C light.

One critical advantage of this invention is the specific utilization of Auger recombination (occurring within the blue/violet InGaN visible light emitting region) as the carrier injection mechanism into the far UV-C emitting region. As operational current or carrier density increases within the LED device, the far UV-C emission power is expected to increase because Auger recombination is known to become more dominant at high current or carrier density.

This device can be modified to emit at any desired UV wavelengths by changing the band gap energy of impurity-doped AlGaN emitting layer by changing the Al composition. In the preferred embodiment, the combination of blue/violet (370 nm-460 nm) and far UV-C light is used. Far UV-C light provides the second critical advantage of this device in contrast to the prior art in UV-C disinfection. Conventional UV-C disinfection emission ranges widely between, for example, 254 nm (mercury lamps) and 265 nm-280 nm (UV-C LEDs). These wavelengths are cataractogenic and carcinogenic for mammalian cells. Because of this, widespread use of disinfecting UV-C light has not been incorporated in public settings. However, there may be alternative embodiments in which conventional UV-C wavelengths are used if desired, without departing from the scope of the present invention.

The target emission wavelength of the preferred embodiment of the present invention is 200 nm-230 nm. In this wavelength region, the light is still harmful to bacteria and viruses [8], while it is harmless for humans. Far UV-C light is so strongly absorbed by the outer layer of dead skin cells that is does not reach any living cells. Similarly, the outer layer of the eye is comprised of dead cells that strongly absorb far UV-C light, thus protecting the cornea, which is the most vulnerable part of the eye. Far UV-C light cannot be efficiently generated using conventional AlGaN-based UV LEDs, because the high Al composition required for far UV-C emission prevents efficient carrier injection and leads to very high operating voltages.

Another advantage is that the structure of this UV-C emitter is similar to conventional InGaN-based violet/blue LED. In the conventional violet/blue LED structure, after the growth of the violet/blue InGaN active layer, a p-AlGaN UV-C emitting layer (active layer) is grown instead of p-GaN. Then, a p-AlGaN cladding layer and p$^{++}$-AlGaN contact layer may be grown. In an alternative embodiment, prior to the growth of the violet/blue InGaN active layer, an n-AlGaN UV-C emitting layer is grown instead of n-GaN. Additionally, an n-AlGaN cladding layer and n$^{++}$-AlGaN contact layer may be grown below the violet/blue InGaN active layer.

There is some lattice mismatch between the proposed far UV-C impurity-doped AlGaN region and the blue/violet InGaN active region. To reduce this mismatch, a Sc-containing material can be used. The Sc-containing nitrides have potential in lattice-matched or nearly-lattice matched device structures. For example, ScAlN can be lattice matched to GaN, AlGaN and InGaN at a wide range of compositions, while having a significant difference in band gap. Furthermore, the ternary ScAlN alloy corresponding to far UV-C emission is nearly lattice matched to GaN and blue/violet InGaN. Lattice engineering using Se-containing nitride layers could thus enable an efficient far UV-C device.

Yet another advantage of the proposed device is that it can replace or supplement conventional white LED fixtures. It may remain an efficient source of white light, with the added benefit of emitting far UV-C light to prevent the transmission of pathogens. The easiest way is that these new far UV-C LEDs with the emission wavelength of 200 nm-230 nm could be installed together with conventional white LED lamp fixtures. In that case, we have to minimize the emission intensity that comes from InGaN violet/blue emission. A filter may need to be utilized to reduce these emissions. These lighting fixtures can be placed in areas where transmission of microbial pathogens is a public health concern such as hospitals, airports, sports arenas, malls, and schools.

Additionally, these fixtures could be used for general lighting everywhere because the coronavirus (COVID-19) pandemic has greatly increased the importance of disinfection applications and 200 nm-230 nm emission does not cause any human health problems. Far UV-C lighting will be extremely effective at preventing pathogens that are airborne-mediated.

The combination of the low cost and small footprint of a semiconductor source (in contrast to a gas lamp source), with the capability of simultaneous visible and UV emission at any desired wavelength, makes the proposed III-nitride device highly favorable.

Modifications

Generally, this invention is applicable to any device comprised of a III-nitride-based UV light emitting structure, wherein a large energy bandgap material is grown on or above or below a small energy bandgap material. For example, the large energy bandgap material is an AlGaN-based material and the small energy bandgap material is an InGaN-based material.

The large energy bandgap material is an emitting layer or active layer of the structure. For example, the large energy bandgap material is a p-type or n-type layer.

The small energy bandgap material generates high energy carriers through Auger processes that are injected into the large energy bandgap material, wherein the high energy carriers recombine to emit UV light.

REFERENCES

The following publications are incorporated by reference herein:

1. Kioupakis E. et al. First-Principles Calculations of Indirect Auger Recombination in Nitride Semiconductors. Phys. Rev, B, 92, 035207 (2015). doi:10.1103/PhysRevB.92.035207.

2. Shen Y, et al. Auger Recombination in InGaN Measured by Photoluminescence. Appl. Phys. Lett. 91, 141101 (2007), doi:10.1063/1.2785135.

3. Iveland J, et al. Direct Measurement of Auger Electrons Emitted from a Semiconductor Light-Emitting Diode under Electrical Injection: Identification of the Dominant Mechanism for Efficiency Droop. Phys. Rev. Lett. 110, 177406 (2013). doi:10.1103/PhysRevLett.110.177406.

4. Buonanno M. et al. 207-nm UV Light—A Promising Tool for Safe Low-Cost Reduction of Surgical Site Infections. I: In Vitro Studies. PLoS ONE 8(10): e76968 (2013). doi:10.1.371/journal.pone.0076968.

5. Buonanno, M. et al. Germicidal Efficacy and Mammalian Skin Safety of 222-nm UV Light. Radiat. Res. 187, 483-491 (2017). doi:10.1667/rr0010cc.1.

6. Zhang J. et al. Transparent deep ultraviolet light-emitting diodes with a p-type AlN ohmic contact layer. Proc. SPIE 10940, Light-Emitting Devices, Materials, and Applications, 1094002 (2019). doi:10.1117/12.2506918.

7. Zhang J. et al. Polarization Electric Field Assisted Hole Supplier and P-type Contact Structure, Light Emitting Device and Photodetector Using the Same. U.S. Pat. No. 10,276,746 B1 (2019).

8. Welch D. et al. Far-UVC Light: A New Tool to Control the Spread of Airborne-Mediated Microbial Diseases. Sci. Rep. 8, 2752 (2018). doi:10.1038/s41598-018-21058-w.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A device, comprising:
a III-nitride-based light emitting structure having both a visible light emitting region and an ultraviolet (UV) light emitting region, wherein:
the visible light emitting region is an InGaN active region emitting violet and/or blue light;
the UV light emitting region is an impurity-doped AlGaN and the impurity-doped AlGaN comprises one or more p-type or n-type AlGaN layers; and
Auger recombination processes lead to generation of high-energy hot carriers in the InGaN active region and the hot carriers transport into the impurity-doped AlGaN layers where the hot carriers recombine to emit UV light.

2. The device of claim 1, wherein the InGaN active region has an emission wavelength of 370 nm-460 nm.

3. The device of claim 1, wherein the InGaN active region is a single quantum well (SQW).

4. The device of claim 3, wherein the SQW has a thickness of less than 5 nm.

5. The device of claim 1, wherein a p-side of the III-nitride-based light emitting structure includes a p-type AlGaN cladding region with a wider band gap than the UV light emitting region formed on or above the UV light emitting region.

6. The device of claim 1, wherein an n-side of the III-nitride-based light emitting structure includes an n-type AlGaN cladding region with a wider band gap than the UV light emitting region formed below the visible light emitting region.

7. The device of claim 1, wherein a p-side of the III-nitride-based light emitting structure includes a p-side contact region formed on or above the UV light emitting region, and the p-side contact region is a highly Mg doped p++-AlGaN region, a p++ GaN region, or a p++-AlN hole-gas.

8. The device of claim 1, wherein the UV light emitting region has an emission wavelength below 310 nanometers (UV-B).

9. The device of claim 1, wherein the UV light emitting region has an emission wavelength below 280 nanometers (UV-C).

10. The device of claim 1, wherein the UV light emitting region has an emission wavelength between 200-230 nanometers (far UV-C).

11. A method, comprising:
fabricating a III-nitride-based light emitting structure having both a visible light emitting region and an ultraviolet (UV) light emitting region, wherein:
the visible light emitting region is an InGaN active region emitting violet and/or blue light;
the UV light emitting region comprises impurity-doped AlGaN and the impurity-doped AlGaN comprises one or more p-type or n-type AlGaN layers; and
Auger recombination processes lead to generation of high-energy hot carriers in the InGaN active region and the hot carriers transport into the impurity-doped AlGaN where the hot electrons recombine to emit UV light.

12. A device, comprising:
a III-nitride-based ultraviolet (UV) light emitting structure, wherein:
a large energy bandgap material is grown on or above or below a small energy bandgap material;
the small energy bandgap material is an InGaN-based material;
the large energy bandgap material is an AlGaN-based material;
the large energy bandgap material is an emitting layer or active layer of the structure; and
the small energy bandgap material generates high energy electrons or holes through Auger processes that are injected into the large energy bandgap material where the high energy electrons or holes recombine to emit UV light.

13. The device of claim 12, wherein the large energy bandgap material is a p-type layer.

14. The device of claim 12, wherein the large energy bandgap material is an n-type layer.

15. The device of claim 12, wherein the large energy bandgap material contains at least some scandium.

* * * * *